(12) United States Patent
Roy et al.

(10) Patent No.: US 10,004,482 B2
(45) Date of Patent: Jun. 26, 2018

(54) DEVICE FOR SAMPLING TEAR FLUID (71) Applicant: OPIA TECHNOLOGIES, Paris (FR)

(72) Inventors: Pierre Roy, Paris (FR); Francoise Brignole-Baudouin, Paris (FR)

(73) Assignee: OPIA TECHNOLOGIES, Paris (FR)

( * ) Notice: Subject to any disclaimer, the term of this patent is extended or adjusted under 35 U.S.C. 154(b) by 137 days.

(21) Appl. No.: 14/352,313

(22) PCT Filed: Oct. 17, 2012

(86) PCT No.: PCT/EP2012/070576
§ 371 (c)(1),
(2) Date: Apr. 16, 2014

(87) PCT Pub. No.: WO2013/057142
PCT Pub. Date: Apr. 25, 2013

(65) Prior Publication Data
US 2014/0309554 A1    Oct. 16, 2014

(30) Foreign Application Priority Data

Oct. 17, 2011  (EP) .................................. 11306342

(51) Int. Cl.
*A61B 5/00*    (2006.01)
*A61B 10/00*    (2006.01)

(52) U.S. Cl.
CPC .. *A61B 10/0045* (2013.01); *A61B 2010/0067* (2013.01)

(58) Field of Classification Search
CPC ............ A61B 10/0045; A61B 10/0048; A61B 10/0051; A61B 10/0064; A61B 2010/0067; A61B 2010/0061; A61B 2010/0074; A61B 2010/0077; A61B 2010/008
See application file for complete search history.

(56) References Cited

U.S. PATENT DOCUMENTS

| | | | | |
|---|---|---|---|---|
| 2,470,665 A | * | 5/1949 | Stiehl .................. | A61M 1/0084 600/581 |
| 4,036,232 A | * | 7/1977 | Genese ............... | A61M 1/0009 600/576 |
| 4,207,899 A | * | 6/1980 | Patel .................. | A61M 25/1025 604/100.01 |
| 4,334,538 A | * | 6/1982 | Juhn ................... | A61B 10/0045 433/95 |
| 4,635,488 A | | 1/1987 | Kremer | |
| 4,658,833 A | * | 4/1987 | Stuart ................... | A61B 3/101 600/584 |

(Continued)

FOREIGN PATENT DOCUMENTS

JP          06-070933          3/1994

*Primary Examiner* — Max Hindenburg
(74) *Attorney, Agent, or Firm* — Womble Bond Dickinson (US) LLP (57) ABSTRACT

Device for sampling tear fluid that comprises: an extraction element (202) adapted to be applied on the eye to draw tear fluid therefrom, comprising at least one tube (209) and a distal portion (201) with at least one opening (207), a collection vessel (203), connected to said tube (209), suction means (210) adapted to continuously draw tear fluid from the eye to the collection vessel (203), through the extraction element (202) for a period higher than 10 minutes once the extraction element (202) is in place.

18 Claims, 11 Drawing Sheets

(56) References Cited

U.S. PATENT DOCUMENTS

| | | | | |
|---|---|---|---|---|
| 4,684,362 A * | 8/1987 | Holt | A61B 10/0045 | |
| | | | 600/578 | |
| 4,701,162 A * | 10/1987 | Rosenberg | A61M 25/0009 | |
| | | | 604/103 | |
| 4,791,914 A * | 12/1988 | May | A61M 1/0023 | |
| | | | 600/573 | |
| 4,813,931 A * | 3/1989 | Hauze | A61M 1/0001 | |
| | | | 600/573 | |
| 4,947,841 A * | 8/1990 | Ng | A61M 1/0001 | |
| | | | 128/207.14 | |
| 4,950,247 A * | 8/1990 | Rosenblatt | A61M 1/0052 | |
| | | | 128/202.29 | |
| 4,957,492 A * | 9/1990 | McVay | A61M 1/0056 | |
| | | | 600/573 | |
| 5,720,299 A * | 2/1998 | Theodoru | A61B 10/0291 | |
| | | | 600/573 | |
| 5,772,607 A * | 6/1998 | Magram | A61B 10/0045 | |
| | | | 600/573 | |
| 5,910,110 A * | 6/1999 | Bastable | A61F 9/00736 | |
| | | | 600/398 | |
| 5,919,356 A | 7/1999 | Hood | | |
| 7,175,594 B2 * | 2/2007 | Foulkes | A61B 1/00094 | |
| | | | 600/219 | |
| 7,258,672 B2 * | 8/2007 | Hansson | A61B 5/1427 | |
| | | | 600/581 | |
| 9,066,698 B2 * | 6/2015 | Peters | A61B 5/150503 | |

\* cited by examiner

DEVICE FOR SAMPLING TEAR FLUID

FIELD OF THE INVENTION

The present invention relates to systems, devices, and methods for sampling tear fluid and subsequently analysing it.

BACKGROUND ART

The Human Eye

Figure 1:
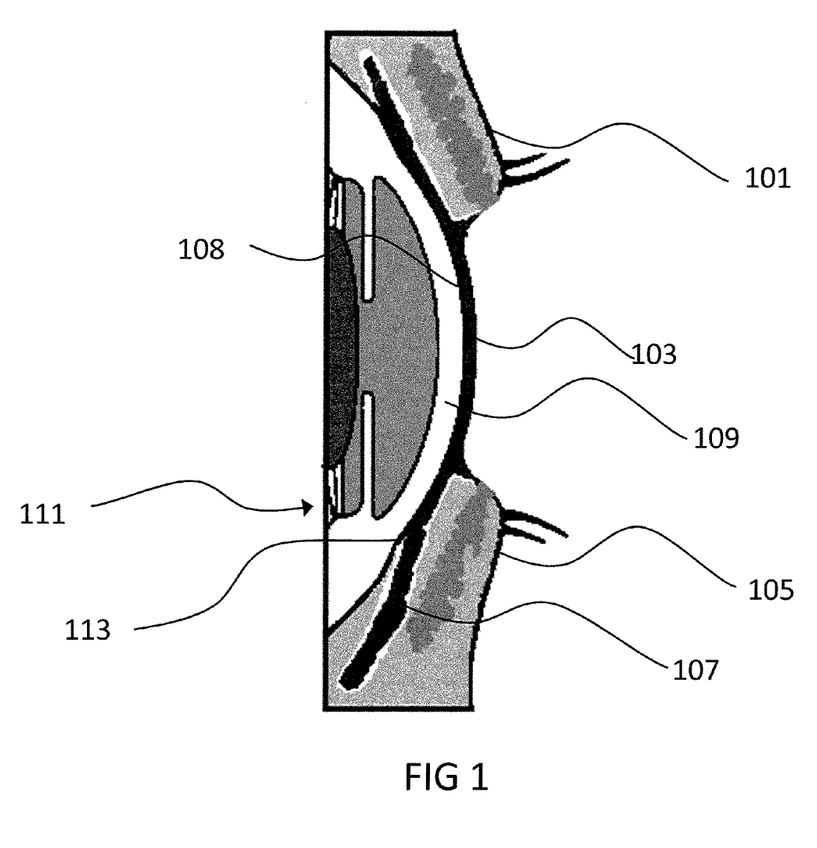
FIG. 1, already commented, is a schematic view of the human eye.

The structure of the ocular surface is described in FIG. 1. The ocular surface comprises:
cornea 109,
conjunctiva 108,
tear film 103, and
upper eyelid 101 and lower eyelid 105.

The cornea 109 is a transparent tissue which role is to catch and focus light on the eye transparent crystalline structure or lens.

The conjunctiva 108 is the outermost layer of the eye 111 and the inner surface of the eyelids 101 and 105. Conjunctiva 108 is covering the white part of the eye 111 or sclera. The limbus 113 is the border of the cornea 109 and the sclera.

Tear film 103 is composed of 2 layers: outermost lipid layer derived from the meibomian glands and innermost aqueous layer composed of lacrimal fluid mixed with soluble mucins. Eyelids 101 and 105 include the lachrymal glands secreting the aqueous component of the aqueous layer (mucins being produced by the goblet cells of the conjunctiva), and the meibomian glands secreting the lipid layer.

Upper eyelid 101 and lower eyelid 105 are the first line of defence of the visible ocular surface, followed by tear film 103. On the last defence lines are the two distinct tissues conjunctiva 108 and cornea 109. The ocular surface is a mucosal transition between the external environment and the fragile intraocular structures. Any condition that reduces the production, alter the composition, or impede the distribution of the tear film 103 may cause noticeable irritations to the structures of the front surface of the eye 111 and a degradation of vision.

These conditions are often related to problems with the structure or function of the eyelids 101 and 105, the conjunctiva 108, or the cornea 109. If not timely and properly diagnosed, and depending upon the severity of symptoms, individuals may be at increased risk of developing secondary infection or chronic inflammation that may not respond to treatment.

Most of the tear fluid is stored in the conjunctival sac 107, which is the transition portion which forms the junction between the posterior surface of the lower eyelid 105 and the surface of the eye 111. The surface of the conjunctival sac 107 is covered by the conjunctiva 108. The bottom of the conjunctival sac 107 is called conjunctival cul-de-sac.

Due to anatomical constraint, a maximum of 30 µl of tear fluid is estimated to be possibly held by the human eye without overflow or spillage. The normal resident tear volume in the eye is approximately 7.5 µl, most of which resides in the conjunctival sacs with approximately 1 µl covering the cornea.

Tear turnover rate in human is about 0.16/min, that is to say that each minute, 16 percent of the tear volume is renewed. It corresponds to around 1.2 µl per minute.

As mentioned before, the structure and composition of the tear film 103 can be divided into two main layers.

The innermost layer in contact with the conjunctiva 108 is the aqueous layer. The aqueous layer is a mixture of lacrimal fluid and different soluble mucins, which are glycosylated proteins.

The aqueous layer is important in that it provides a protective layer and lubrication to prevent dryness of the eye. Dryness of the eye can cause symptoms such as itchiness, burning, and irritation, which can result in discomfort. It is a few micrometers thick.

The outermost lipid layer is comprised of many lipids known as meibum or sebum. This outermost lipid layer is very thin, typically less than 250 nm thick. The lipid layer provides a protective coating over the aqueous layer to limit the rate at which the underlying aqueous layer evaporates. A higher rate of evaporation of the aqueous layer can cause dryness of the eye. The lipid layer also lubricates the eyelids 101 and 105 during blinking, which prevents dry eye.

More generally, in the human eye, the unique structure of the tear film 103 enables it to perform many functions, based on its lipid, and aqueous layer components.

Seven major functions of the tear film 103 are:
Maintaining a smooth surface for light refraction. The tears form the first refractive surface encountered by light on its path to the retina. For clear vision, it is critical to maintain the transparency of the second refractive surface that rays of light encounter, i.e. the cornea 109.
Lubricating the eyelids 101 and 105.
Lubricating the conjunctiva 108 and the cornea 109, thus avoiding ocular surface mechanical damage from the high pressures generated by each blink.
Supplying the cornea 109 with nutrients by transporting oxygen and a limited number of other nutrients to the avascular cornea 109, regulating the electrolyte composition and pH.
Providing white blood cells with access to the cornea 109 and conjunctiva 108.
Removing foreign materials from the cornea 109 and conjunctiva 108. The tear film 103 protects the ocular surface from the external environment by responding dynamically to a wide range of external conditions and potentially damaging situations. These external stresses include desiccation, bright light, cold, mechanical stimulation, physical injury, noxious chemicals, and bacterial, viral, and parasitic infection.
Defending the ocular surface from the pathogens via specific and nonspecific antibacterial substances.
Example of Ocular Surface Diseases and Diagnosis
Dry Eye Disease Dry eye disease, or keratoconjunctivitis sicca (KCS), is a common eye problem that involves irritation and blurry vision caused by damage to the ocular surface by insufficient tear production or excessive tear evaporation and that can affect quality of life. In KCS, one or more of the tear film 103 structure components is present in insufficient volume or is otherwise out of balance with the other components.

It is prevalent in the ageing population, with a higher incidence among women. Although it is a common diagnosis, physicians have to rely on many symptoms and diagnostic tests to confirm its presence.
Schirmer Test and Dry Eye Diseases The Schirmer test estimates the tear volume or secretion. It involves a strip of filter paper partially blocked in the lower conjunctival sac 107, inducing irritation and reflex tearing. The Schirmer test relies on the presence of a good tear meniscus to act as a reservoir from which fluid can be drawn and absorbed by the paper.

Unfortunately, the Schirmer test has many disadvantages, including low reproducibility, sensitivity and specificity, frequent discomfort, difficulty of performing the test in children, potential injury of the conjunctiva 108 and cornea 109, lack of a definite site of paper placement in the conjunctival sac 107, uneven absorption of tear fluid by the paper strip, uncertainty whether the quantity of fluid absorbed by paper strips is directly proportional to the wetted length, difficulty for evaluating the wetting length in cases where the leading edge of the wetted area is round or oblique, and lack of control over reflex lacrimation.

Osmolarity and Dry Eye Diseases

It is known that the fluid tonicity or osmolarity of tears generally increases in patients with KCS. KCS is associated with conditions that affect the general health of the body, such as Sjogren's syndrome, ageing, and androgen deficiency. Therefore, tear film 103 osmolarity can be a sensitive and specific indicator for the diagnosis of KCS and other conditions.

The osmolarity of a sample tear fluid can be assessed by an ex vivo technique called "freezing point depression", taking advantage of the fact that solutes or ions in a solvent cause a lowering of the fluid freezing point from what it would be without the ions. Presently, freezing point depression measurements are made ex vivo by removing tear samples from the eye 111 using a micropipette or a blunt needle and measuring the depression of the freezing point of the sample that results from heightened osmolarity.

However, these ex vivo measurements are plagued by many difficulties. For consistent analysis, a relatively large volume should be collected, at least around 20 μl of tear sample, typically around 60-80 μl. Moreover, corresponding processes according to the state of the art stated above require the presence of medical personnel for about one hour. Tear turnover is approximately 42 percent lower in KCS subject than in normal subject. Hence the need for at least twice the time to collect the necessary amount from KCS subject than for normal subject. Because no more than about 10 to 100 nL of tear sample can be obtained at any one time from a KCS subject, the collection of sufficient amounts often requires a physician to induce reflex tearing in the subject. Reflex tears are more dilute, i.e. have fewer solute ions than normal tear fluid. In some cases, reflex tearing produce false negatives.

False negatives may also result from the inherent metastability of the tear film 103 of KCS subject. This metastability, punctuated by periods of hyperosmolarity may be explained by the subject compensatory mechanisms, such as increased blinking and reflex stimulations of the eye glands, punctually subdued by breakdowns. Any dilution of the tear film 103 or reunion of samples taken at different times invalidates the diagnosis of an osmolarity test for KCS and therefore makes currently available ex vivo methods prohibitive in a clinical setting.

The absolute validity of an osmolarity based KCS diagnosis is hence in itself to be questioned as the statistic osmolarity profiles of KCS subjects and normal subjects overlap each other, resulting in a zone of non-robust diagnosis, as described in "Tear Film Osmolarity: Determination of a Referent for Dry Eye Diagnosis" by Tomlinson et al. in "Investigative Ophthalmology a Visual Science" 47 (2006) 4309-4315.

Allergy

Allergic diseases of the conjunctiva are a common and heterogenous group disorders characterized by the expression of a classical type 1 IgE-mediated hypersensitivity reaction at the conjunctival level.

IgE is a subclass of immunoglobulin and is involved in the pathophysiology of severe type 1 hypersensitivity allergic reaction. IgE is detected in circulatory blood and somatic tissues. IgE in tissues binds to the IgE receptor expressed mainly on mast cells. Clinical examinations to detect IgE are classified into two methods: determination of total IgE and determination of antigen-specific IgE in serum. Total IgE in serum reflects systemic atopic diathesis and antigen-specific IgE indicates the presence of a sensitized antigen.

As described in "Clinical Evaluation of Total IgE in Tears of Patients with Allergic Conjunctivitis Disease Using a Novel Application of the Immunochromatography Method" by Inada et al. in "Allergology International" 58 (2009) 585-589, for many allergic disorders, such as allergic conjunctivitis, eye-specific immune reaction is considered to be critical in the pathogenesis.

To investigate the eye-specific immunological disorders in allergic diseases, examination of total IgE in tears might be a better marker to assess the tissue-specific pathophysiology rather than serum IgE examination. Therefore, an examination of total IgE in tears is useful not only for the diagnosis but also for the assessment of allergic conjunctivitis diseases severity.

For example, total IgE serum levels are significantly increased in vernal KCS than in controls. However, IgE levels are variable among subjects with ocular allergy and cannot be used as a reliable indicator of disease activity or severity.

Studies investigating allergen-specific serum IgE levels have detected a range of allergen specificities. Allergen specific IgE is also increased in tear samples and there is a highly significant correlation with ocular allergy symptoms, supporting a diagnostic value for specific tear IgE, although limitations in volume of above described tear sampling methods restrict its use in routine immunoassays.

Proteomics

Human tear fluid is shown to have more than 600 proteins, among which 491 proteins have been duly identified. The tear proteins play an important role in maintaining the ocular surface, and changes in tear protein composition may reflect the changes in the health of the ocular surface.

The relative proportions of the proteins present in a subject tear sample, that is to say its tear fluid proteomic profile, depend on the method of tear collection. Invasive methods, including filter paper and cellulose sponges, stimulate the conjunctiva 108, induce serum leakage, and result in a higher proportion of plasma proteins. Samples collected by less invasive means, such as fine capillary tubes dipped into the tear meniscus, demonstrate a higher proportion of lacrimal gland proteins.

As described in "Comparative proteomics of human male and female tears by two-dimensional electrophoresis" by Ananthi et al. in "Experimental Eye Research" 92 (2011) 454-463, proteomic analysis of tear fluid shows promising results for eye diseases diagnostic.

Tear fluid analysis can be based on noninvasive approaches in early diagnosis and study of pathogenesis of eye-related diseases. It may also assist follow-up assessment of therapeutic treatment. For some eye diseases such as KCS, the development of new potential treatments is hampered by the fact that there are no objective criteria available to precisely assess the treatment.

A standard tear proteomic pattern from healthy individuals may serve as a reference to measure the success of treatment. Tear proteome profiling can also generate useful information for the understanding of the interaction between an eye and its contacting objects, such as a contact lens or a lens implant. This is important for designing improved eye-care devices and maintaining the health of an eye.

As described in "Diagnostic biologique des conjonctivites" by Batellier et al. in "EMC, Ophtalmologie" 21-130-B-10 (2010), IgE and proteomic analyses may provide consistent diagnoses, provided a sufficient amount of tear fluid can be collected.

U.S. Pat. No. 7,810,380 discloses a system and method for collecting tear film 103 and measuring tear film 103 osmolarity that requires only a small amount of tear film 103, typically around 20 nL. But this method requires a system that is expensive and complicated to produce, and this system requires the presence of a physician for being used. Moreover, the validity of a diagnosis that depends on a measurement performed on such a small amount of tear fluid sampled at a precise moment is questioned. A gradient of composition exists within the few micrometers thick tear film 103, and the composition also differ within the tear meniscus. This results in different osmolarity measures depending on the exact spot, position of sampling, as well as the pressure applied and the angle of the device chosen by the person manipulating the device. The gradient is therefore questioning the reproducibility of such a test. A diagnosis resulting from such a sample hence strongly depends on the circumstances of the time of the sampling, and may not represent the eye state.

RU2335233 discloses a device for tear collection. However this device does not solve tear sampling main problems in that it just allow to collect tear fluid already evacuated from the eye and does not prevent evaporation during tear sampling that will modify the tear composition.

Thus, current sampling techniques are of questioned reproducibility or unavailable in a clinical setting and can't attain the volumes necessary for many ocular surface disorders diagnostics, typically 60-80 μl. Even if the amount was reached, the necessary time would induce evaporation effect, thus impairing the quality of the sample. There is also a risk of corneal or conjunctival injury or irritation of the conjunctiva 108 due to the repetitive use of collection devices such as capillary tubes, surgical sponges or tear strips.

Hence the need for an improved and clinically feasible sampling technique.

SUMMARY OF THE INVENTION

The invention concerns a device for sampling tear fluid, comprising:
  an extraction element adapted to be applied on the eye to draw tear fluid therefrom, comprising at least one tube and a distal portion with at least one opening,
  a collection vessel, connected to said tube,
  suction means adapted to continuously draw tear fluid from the eye to the collection vessel, through the extraction element for a period higher than 10 minutes once the extraction element is in place.

Advantageously albeit optionally, the device according to the invention includes one or any possible combination of the following features:
  the extraction element is adapted to extend in the conjunctival sac and to remove tear fluid which resides into the conjunctival sac,
  the distal portion comprises an outer rim, said outer rim being adapted to be positioned on the surface of the eye situated under the lower eyelid,
  the distal portion includes the collection vessel which is reservoir shaped,
  the extraction element is a flexible catheter having a distal portion presenting perforations,
  the distal portion of the extraction element has a thickness that ranges between 0.5 and 3 mm and has a part adapted to be in contact with the curvature of the eye in that the part presents a radius of curvature that ranges between 10 and 14 mm,
  the collection vessel comprises a first vessel opening allowing in tear fluid from the extraction element and a second vessel opening linked to the suction means drawing air out, said second vessel opening being adapted not to allow tear fluid out,
  the collection vessel is a microfuge tube and/or has an internal volume higher than 20 μL, preferably higher than 80 μL,
  the collection vessel includes the suction means in that the collection vessel is evacuated before the sampling,
  the collection vessel comprises fastening means adapted to fasten said collection vessel on the face of the subject, in the vicinity of the temporal palpebral fissure,
  the sampling device comprises a vacuum gauge,
  the suction means comprise a pump,
  the suction means comprise a three ways non-return valve, one non-return way allowing air from the collection vessel and one other non-return way drawing air out of said valve, last way being linked to a plunger assembly, said plunger assembly being successively pushed and pushed back.

The invention also comprises a method of tear fluid analysis realized by means of a device according to the invention, comprising:
  a step of placing the extraction element on the eye of the subject,
  a step of continuous sampling of tear fluid by said device for a period higher than 10 minutes once the extraction element is in place, the sampled tear fluid being stored in a collection vessel,
  a step of removing the extraction element,
  a step of analysis of the sample, the step of analysis of the sample being performed during and/or after the step of continuous sampling of tear fluid.

Advantageously albeit optionally, the method according to the invention includes one or any possible combination of the following features:
  the step of analysis comprises an osmolarity analysis,
  the step of analysis comprises an IgE analysis,
  the step of analysis comprises a proteomic analysis.

The invention presents numerous vantages.

It provides a tear sampling device that does not have the above-mentioned drawbacks.

It provides a tear sampling device that is more effective, and that makes it possible to optimize the quantity of tears extracted and the quality thereof.

It provides a device that is simple, inexpensive, and safe to manufacture and to use, in particular with regard to sterility and risk of altering the sample by evaporation.

It provides an easy to process method and system for sampling tear fluid that requires minimal medical personnel presence and little human intervention. It provides a reproducible method and system of tear sampling that enables several trustful eye disease diagnoses techniques to be used, in particular for KCS and allergies diagnoses.

BRIEF DESCRIPTION OF THE DRAWINGS

The above and other objects, features and advantages of this invention will be apparent in the following detailed description of an illustrative embodiment thereof, which is to be read in connection with the accompanying drawings wherein:

FIGS. 8a and 8b represent two methods of tear fluid analysis In the following description, the references related to space localization relates to the position of the device when placed on the eye for tear sampling. In all figures, similar elements have identical numeric references.

DETAILED DESCRIPTION OF PREFERRED EMBODIMENTS

Example of Embodiment

Figure 2:
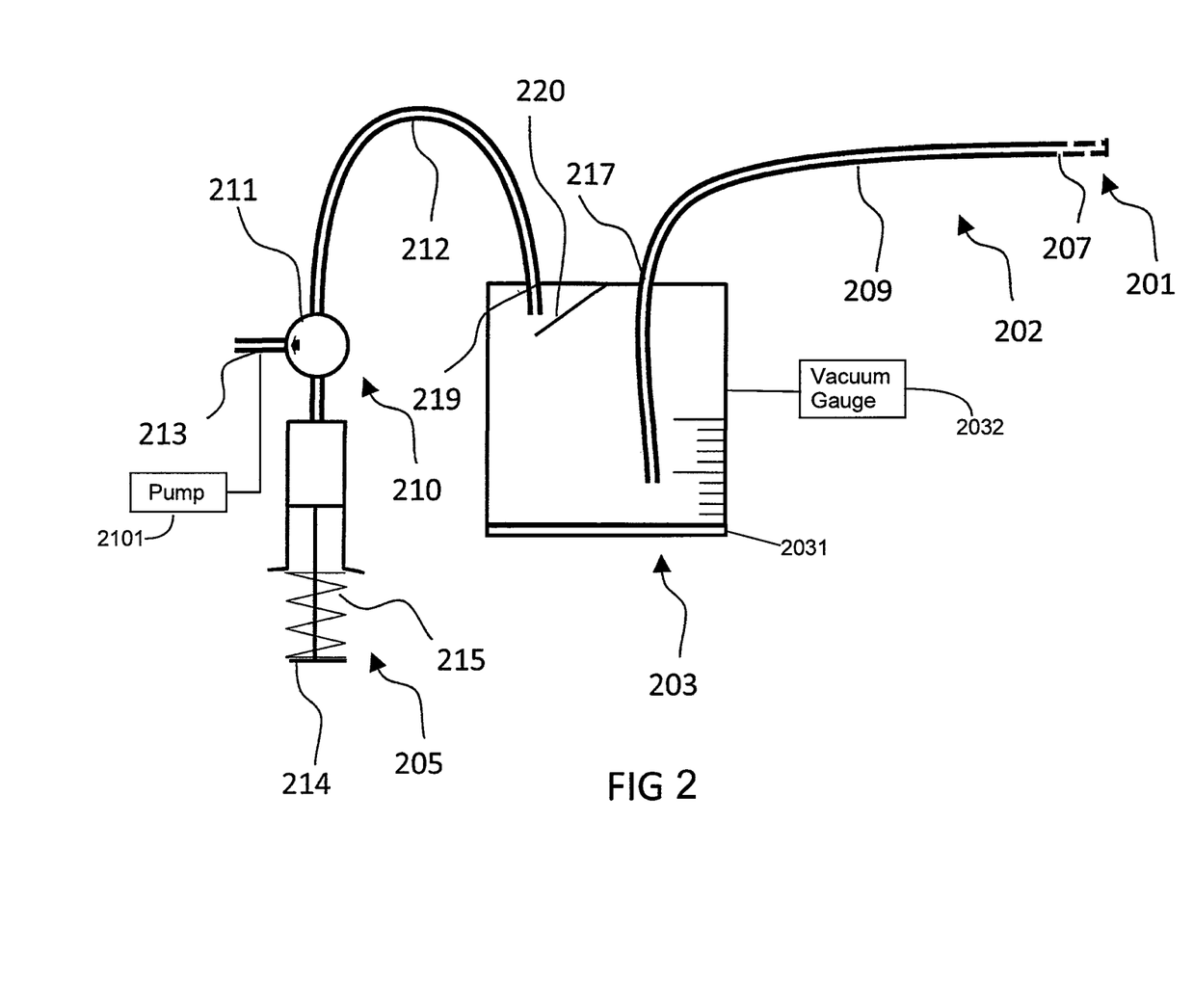
FIG. 2 is a schematic representation of an example of a tear sampling device.

An example of device for sampling tear fluid is represented by FIG. 2. The device is adapted to be applied on the ocular surface to draw tear fluid therefrom for a period of ten minutes, twenty minutes, forty minutes or one hour, once the extraction element is in place. The sampling can last longer than one hour without any change in the device.

The sampling device comprises an extraction element 202 adapted to be applied on the surface of the eye 111, a collection vessel 203 connected to said extraction element 202, and suction means 210.

In this example, the extraction element 202 comprises a flexible tube 209, for instance a flexible catheter with a distal portion 201. The tube 209 is adapted to be inserted in a cavity of the eye, for example the conjunctival sac 107. The tube 209, which insertion is facilitated by its small size, is made of biocompatible materials or materials suitable for medical application.

The distal portion 201 of the catheter is adapted to be placed in the conjunctival sac 107 to extract tear fluid therefrom. For this purpose, it contains at least one opening, or several openings 207, for instance on its edge, to optimize the sampling. Openings can be holes, but can as well be slits, cuts, or V-shaped cuts. The distal portion 201 can be the end of the tube, but can also be of many shapes and the openings placed in many different fashions according to the knowledge of the man skilled in the art.

The collection vessel 203 can be any receptacle suited for storing tear fluid in suited conditions, provided it protects the sample from unwanted contamination that would spoil it and would increase the risk of erroneous results to the test it is meant to be subject to. In this example, the sampling can be subject to osmolarity test, IgE tests and tests concerning proteomics.

The collection vessel 203 is linked to the extraction element 202. In FIG. 2, the connection is ensured by the tube 209. The collection vessel 203 is adapted to be linked to suction means 210.

In FIG. 2, the collection vessel 203 is a small container, having for instance a capacity of 100 μL to a few milliliters, such as a microfuge tube, provided it can be connected to the extraction element 202 and suction means 210.

The collection vessel 203 can placed in a cooling device, either after the sampling or during the sampling, in order to ensure conservation of the sample composition, especially proteins composition. The cooling has for instance its temperature regulator set on 4° C.

The collection vessel 203 is pierced with two vessel openings 217 and 219; the first vessel opening 217 is adapted for the connection to the extraction element 202 by the tube 209. The second vessel opening 219 is adapted for the connection to the suction means 210. For this purpose, it can be protected by a flange 220 that prevents fluid from being absorbed by the suction means 210.

Both connecting vessel openings 217 and 219 are designed in order to avoid any contamination of the sampled tear fluid. For that purpose, both vessel openings 217 and 219 can be secured by joints.

The collection vessel 203 can comprise fastening means 2031 adapted to fasten the collection vessel on the face of the subject, in the vicinity of the temporal palpebral fissure. Fastening means can be understood as a fastener. Fastening means can be adhesive gels, double-side tape, a device comprising an elastic or adhesive band, or any suited other means for fastening, sticking or binding according to the knowledge of the man skilled in the art. Such fastening means reduce the dead volume generated in the tube 209 by reducing its length. Fastening means also allow a greater mobility of the subject during the sampling.

The suction means 210 described in FIG. 2 comprise a three ways non-return valve 211. The valve 211 can accept air coming through a vacuum tube 212 from the collection vessel 203 in a non-return way. It can as well expel air to an exhaust tube through a second non-return way. The third way is linked to a plunger assembly 205 such as a syringe which comprises a plunger 214 and a spring 215 for pushing back the plunger 214 after it has been manually pushed. The plunger assembly 205 is devised so that when the plunger 214 is pushed back by the spring 215, it will create enough vacuum to initiate the sampling, that is to say the extraction of the tear fluid from the conjunctival sac 107. Pushing the plunger 214 forces the air stored into the plunger assembly 205 through the second non-return valve of the valve 211 and an exhaust tube 213. Release of the plunger 214 pushed back by the spring will draw air from the collection vessel 203 through the vacuum tube 212. Pushing and releasing the plunger 214 several times in a row will increase the level of vacuum into the collection vessel 203 up to a level adapted to the patient and the sampling procedure. Such procedure does not require the presence of medical personnel.

Suction means 210 are hence adapted to drop the pressure to a value around 10 mbar to 100 mbar under atmospheric pressure.

More generally, the suction means 210 are devised to perform a long term sampling with minimal human interaction, in particular no medical personnel specific intervention between the moment the device is placed and the moment it is removed. For this purpose, the suction means 210 work at a smooth and continuous pace, in a sense that the device may be able to sample continuously for a duration that may be comprised between minutes and hours. The suction means 210 are different from pipetting, the latter not working in a continuous way, but an incremental one. The suction means 210 are devised to take into account the fact that the suction will be applied to an eye part for an extended period of time.

For this purpose, the suction means 210 can comprise any adapted vacuum regulator known by the man skilled in the art, such as a vacuum control valve. The suction means 210 can be other kinds of valves, or comprise a tare adapted to limit the suction level. The suction means 210 can comprise a bellow.

The suction means 210 can comprise a pump 2101 suited for extracting such quantities of fluid at the desired speed; for instance linear or 360 degree peristaltic pumps, scroll pumps, diaphragm pumps.

The suction means 210 can be a vacuum container, that is to say a device or container provided with a prevacuum level. In that case, suction means 210 can also be connected directly to the drain and be the collection vessels 203 provided with a prevacuum level.

The collection vessel 203 or the suction means 210 can also comprise a passive suction control device which is not represented in the figures. The passive suction control device can be a vacuum gauge 2052. The vacuum gauge ensures visual control of the suction level, so that it can be increased if too low. The vacuum gauge can comprise a bellow.

Other Examples of Distal Portions

Other possible distal portions 201 are shown in FIGS. 3a, 3b, 4a, 4b, 5a, 5b, 5c, 5d,6, 7a and 7b.

The form of the distal portion 201 is adapted to the morphology of the eye part it is in contact with. The distal portion 201 has a part adapted to the form of the eye 111 curvature.

The dimensions of the distal portion 201 are therefore adapted to the size of the eye 111. An adult human eye has a volume of 5.5 ml and an anteroposterior diameter of 24 mm. As these dimensions are stable in the human population and reached quite early, standard dimensions of the distal portion 201 can be defined.

The configuration of the part of the distal portion 201 in contact with the ocular surface, has a general radius r of curvature of about 12 mm and a thickness of about 1 mm.

The radius r of curvature can range between about 10 and 14 mm. The thickness of the distal portion 201 can range between about 0.5 and 3 mm.

The distal portion 201, a catheter end, advantageously comprises a material having a Shore A hardness ranging between 5 and 60, and preferably between 5 and 25, to avoid irritation of the conjunctiva 108.

Distal portions 201 represented in FIGS. 3a, 3b, 4a and 4b comprise an outer rim 701 and a pierced part 702.

Figure 3A:
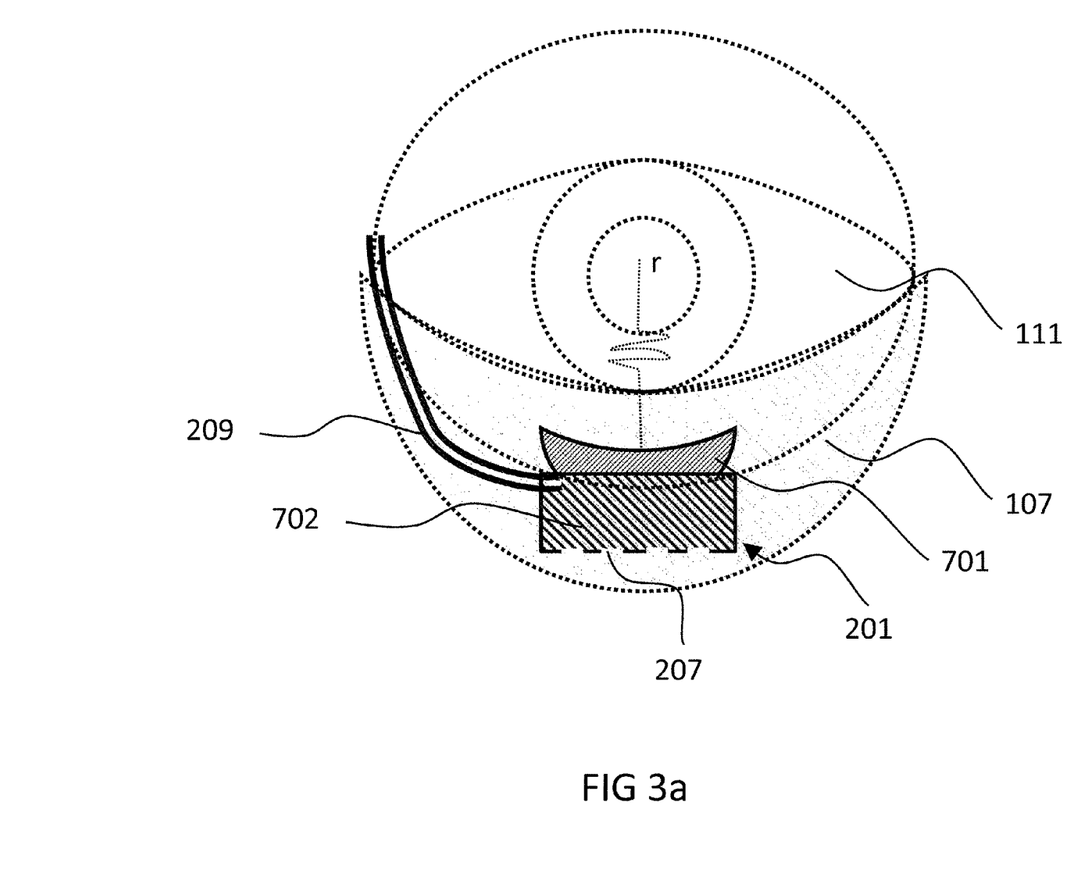
FIGS. 3a, 3b, 4a, and 4b represent two possible distal portions of a tear sampling device comprising an outer rim.
Figure 3B:
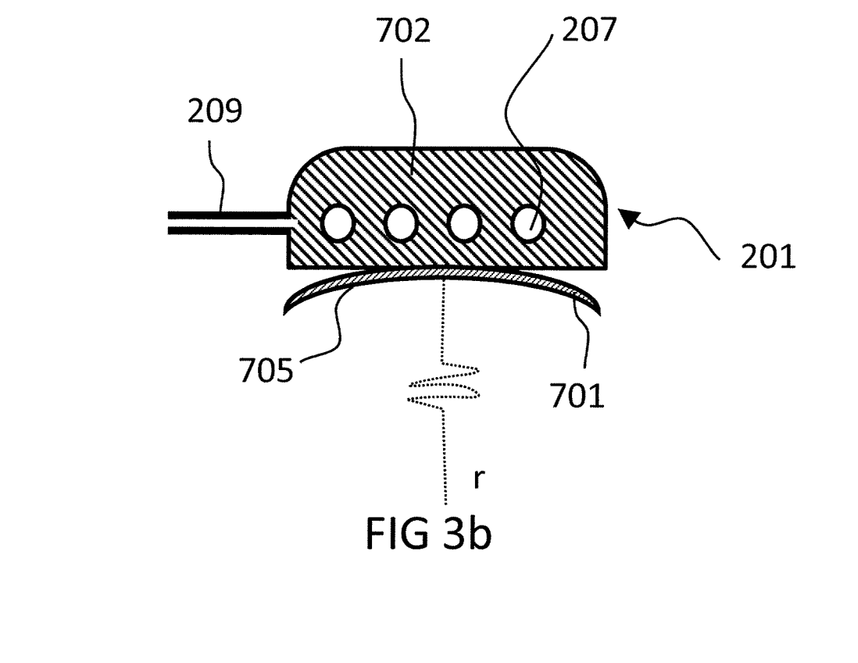

FIGS. 3a and 3b schematically represent two different views of one distal portion 201. FIG. 3a shows the distal portion 201 positioned in the conjunctival sac 107. In FIG. 3b, the distal portion 201 is represented from below. The horizontal section of the pierced part 702 has a shape of a rectangle with two rounded angles, the rounded angles being oriented toward the lower eyelid 105. The vertical section of the pierced part 702 is a rectangle. The lower longer side of the pierced part 702 is pierced with perforations which works as openings 207 that allow tear fluid to be extracted.

The distal portion 201 is to be placed so that openings 207 are facing the conjunctival cul-de-sac of the conjunctival sac 107.

The distal portion 201 is linked to the collection vessel 203 through the tube 209 that extends sideways, orthogonally from the upper part of a smaller side wall of the pierced part 702. The tube 209 connexion to the distal portion 201 is placed so that it exits the conjunctival sac 107 through the extremity of the lower eyelid 105 located next to the lateral palpebral fissure.

Figure 4A:
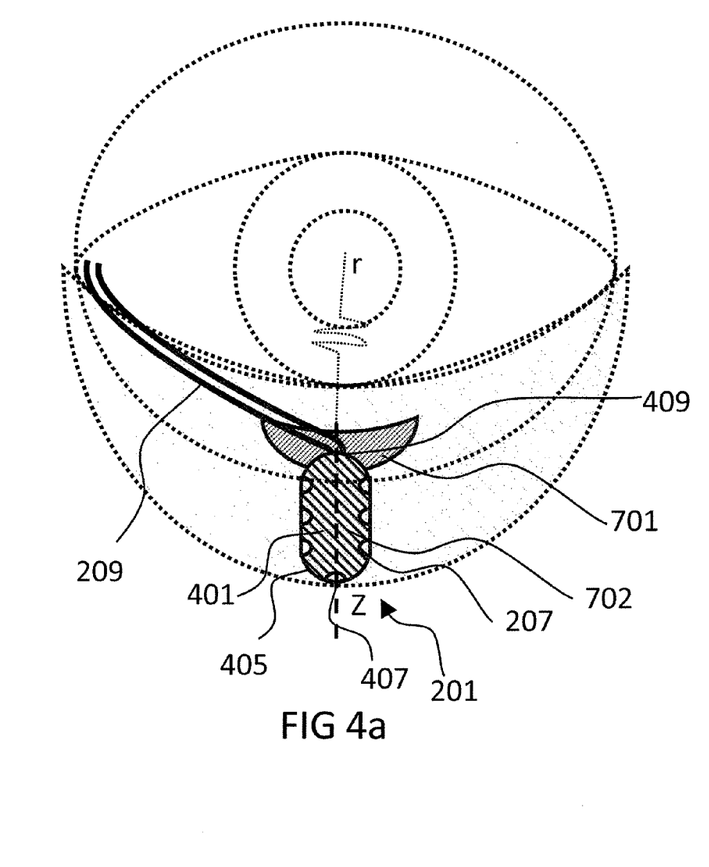
Figure 4B:
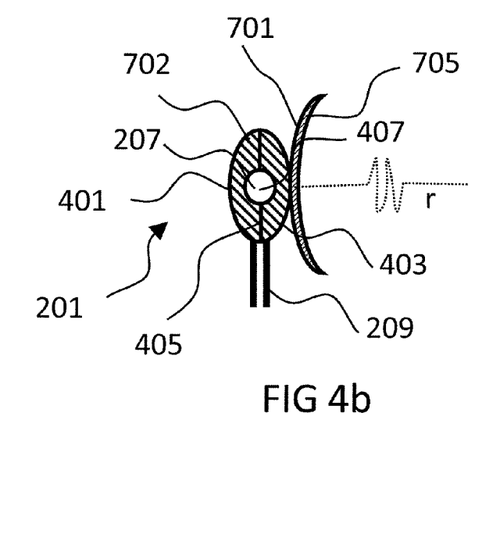

FIGS. 4a and 4b schematically represent two different views of one another distal portion 201. FIG. 4a shows the distal portion 201 positioned in the conjunctival sac 107. In FIG. 4b, the distal portion 201 is represented from below.

The shape of the pierced part 702 of the distal portion is that of a flattened oval, oriented according to an approximately vertical Z axis, the flattened oval thus presenting a lower extremity 407 and an upper extremity 409. The pierced part 702 has oval shaped horizontal and vertical sections, the pierced part 702 being taller than larger. Due to the vertical orientation of the flattened oval shaped pierced part 702, its maximum length is the medium vertical length, which is the length joining the lower extremity 407 and the upper extremity 409. The pierced part 702 is thus formed of two rather flat lateral walls 401 and 403 joined by a circumferential edge line 405 determining the contour of the medium length vertical section of the pierced part 702. When the device is positioned, the outer lateral wall 401 faces the lower eyelid 105 while the inner lateral wall 403 faces the surface of the eye 111 situated under the lower eyelid 105.

The pierced part 702 is pierced with openings 207 on the edge line 405, in particular on the lower extremity 407. The tube 209 connexion is located on the pierced part 702 upper extremity 409. The tube 209, flexible, exits the conjunctival sac 107 through the extremity located next to the lateral palpebral fissure.

Distal portions 201 represented in FIGS. 3a, 3b, 4a and 4b each comprise an outer rim 701.

The outer rim 701 is to be placed upon the surface of the eye 111, more precisely on the surface of the eye 111 situated under the lower eyelid 105. The outer rim 701 allows the surface of the eye 111 not to be hurt by other parts of the extraction element 202. The outer rim 701 is concave, has the shape of a flattened crescent with an inner side 705 complementary to the surface of the eye 111 situated under the lower eyelid 105. For this purpose, the outer rim 701 has a curvature similar to that of the surface of the eye 111 situated under the lower eyelid 105. The outer rim has a general radius r of curvature that is the distal portion 201 radius r of curvature according to the description given above.

FIGS. 5a, 5b, 5c and 5d represent a distal portion 201 without an outer rim 701. The distal portion 201 has a vertical section in the shape of a circular sector, the vertexes of all circular sector shaped vertical sections forming an upper vertex edge 501 of the distal portion 201, the upper vertex edge 501 being curved and having a radius r curvature as described above. The end of the tube 209 is linked to one end of the upper vertex edge 501. Opposite the upper vertex edge 501 is a lower arcuate side 503 which is formed by the arcs of all circular sector shaped vertical sections. The lower arcuate side 503 presents the same curvature as the upper vertex edge 501. The lower arcuate side 503 bears openings 207, meant to be directed downwards, towards the conjunctival cul-de-sac of the conjunctival sac 107.

Figure 5A:
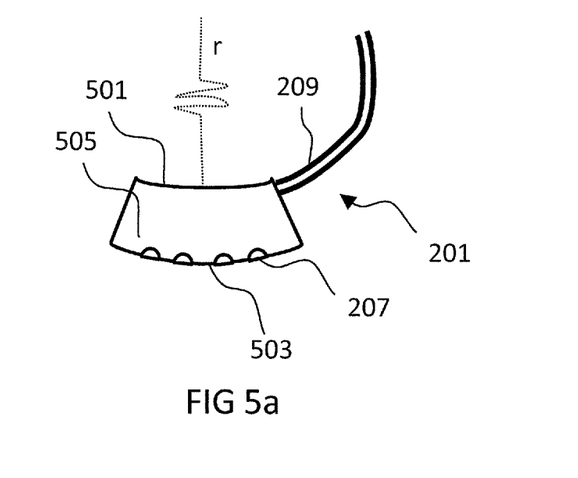
FIGS. 5a, 5b, 5c and 5d represent one other possible distal portion of a tear sampling device without an outer rim.
Figure 5B:
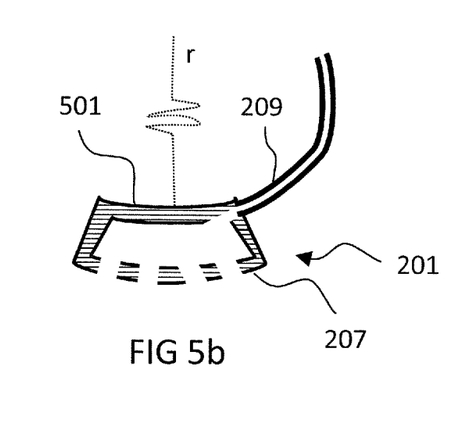
Figure 5C:
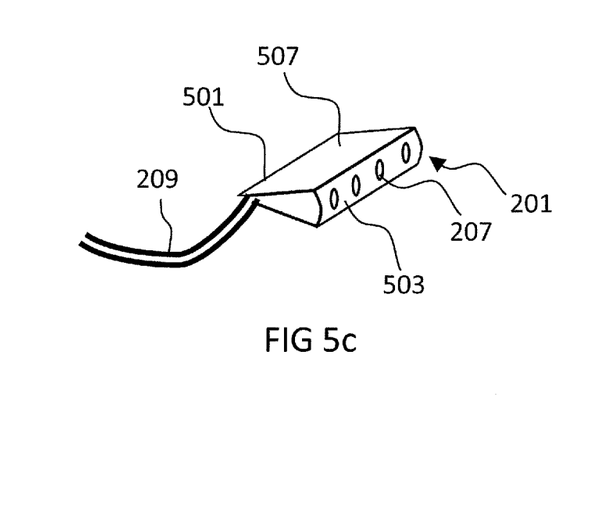

The distal portion 201 comprises four lateral sides, two circular sector sides facing each other and two annular sector sides 505 and 507 facing each other. The common upper arc of the two annular sector sides 505 and 507 is the upper vertex edge 501. The outer annular sector side 505 faces the lower eyelid 105 while the inner annular sector side 507 faces the surface of the eye 111. FIG. 5a represents a front view of the distal portion 201 showing the outer annular sector side 505. FIG. 5b represents a vertical section of the distal portion 201 from the same point of view, the distal portion 201 being essentially hollow and linked to the collection vessel 203 by the tube 209. FIG. 5c is a perspective view of the distal portion 201.

Figure 5D:
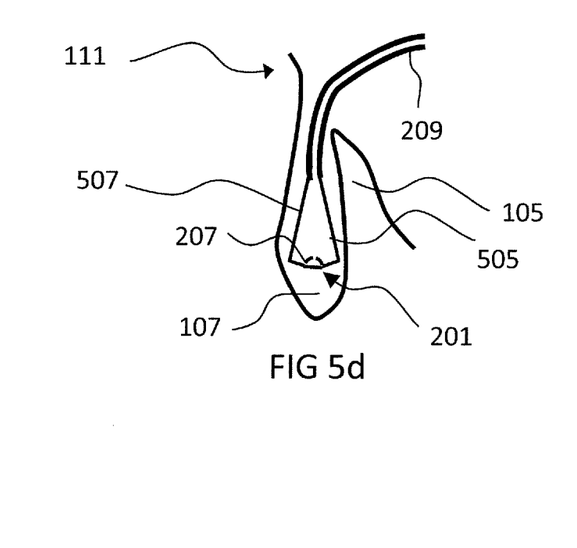

FIG. 5d represents the distal portion 201 placed within the conjunctival sac 107, where the openings 207 are directed downwards, toward the conjunctival cul-de-sac of the conjunctival sac 107, while the upper vertex edge 501 is directed toward the top of the conjunctival sac 107.

Figure 6:
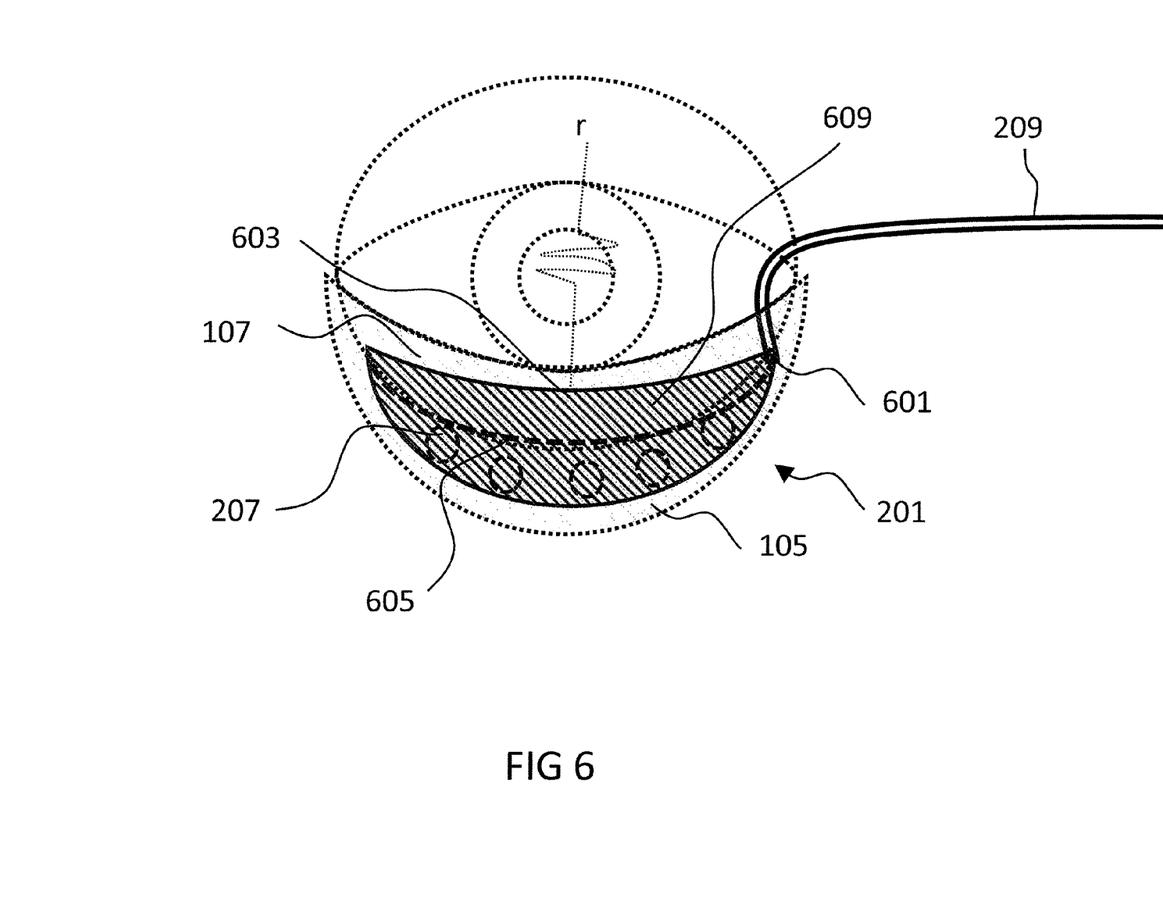
FIG. 6 represents another possible distal portion of a tear sampling device without an outer rim.

Another distal portion 201 without an outer rim is shown in FIG. 6 located within the conjunctival sac 107. The distal portion 201 is curved and crescent shaped. The distal portion 201 presents two lateral curved sides 607 and 609, one inner curved side 607 facing the surface of the eye 111 situated under the lower eyelid 105 and one outer curved side 609 facing the lower eyelid 105. The inner curved side 607 and outer curved side 609 curvatures are chosen in order to correspond respectively to the curvature of the surface of the eye 111 situated under the lower eyelid 105 and to the curvature of the posterior surface of the lower eyelid 105. The junction between the two lateral curved sides corresponds to an upper crescent edge 603 and a lower crescent edge 605. Openings 207 are pierced alongside the lower crescent edge 605, on the outer curved side 609. The distal portion 201 is linked to the collection vessel 203 through a flexible tube 209 such as a flexible catheter. The tube 209 is connected to the distal portion 201 at the level of a horn 601 of the crescent shaped distal portion 201. The horn 601 is located next to the lateral palpebral fissure.

Figure 7A:
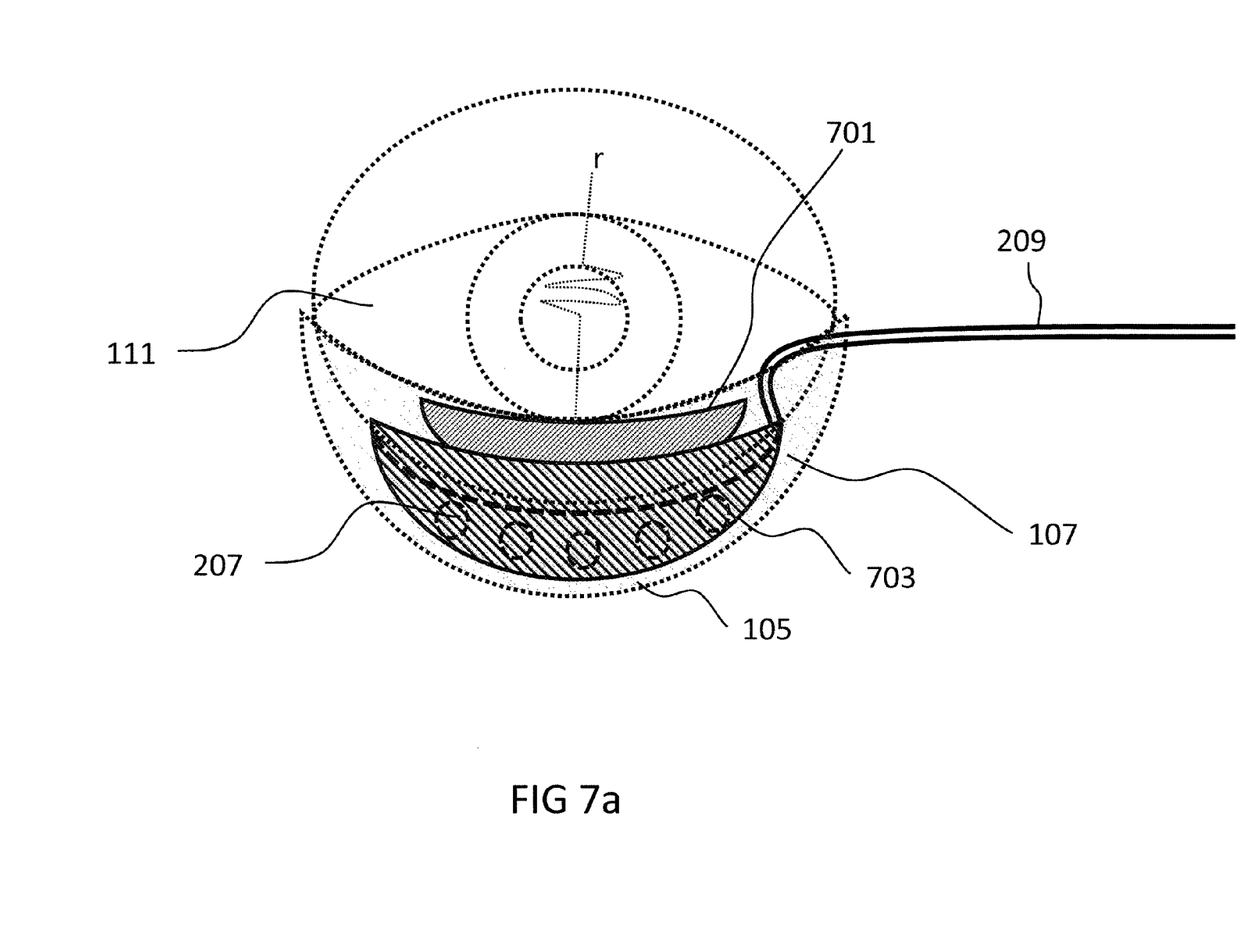
FIGS. 7a and 7b represent a similar distal portion augmented with an outer rim.
Figure 7B:
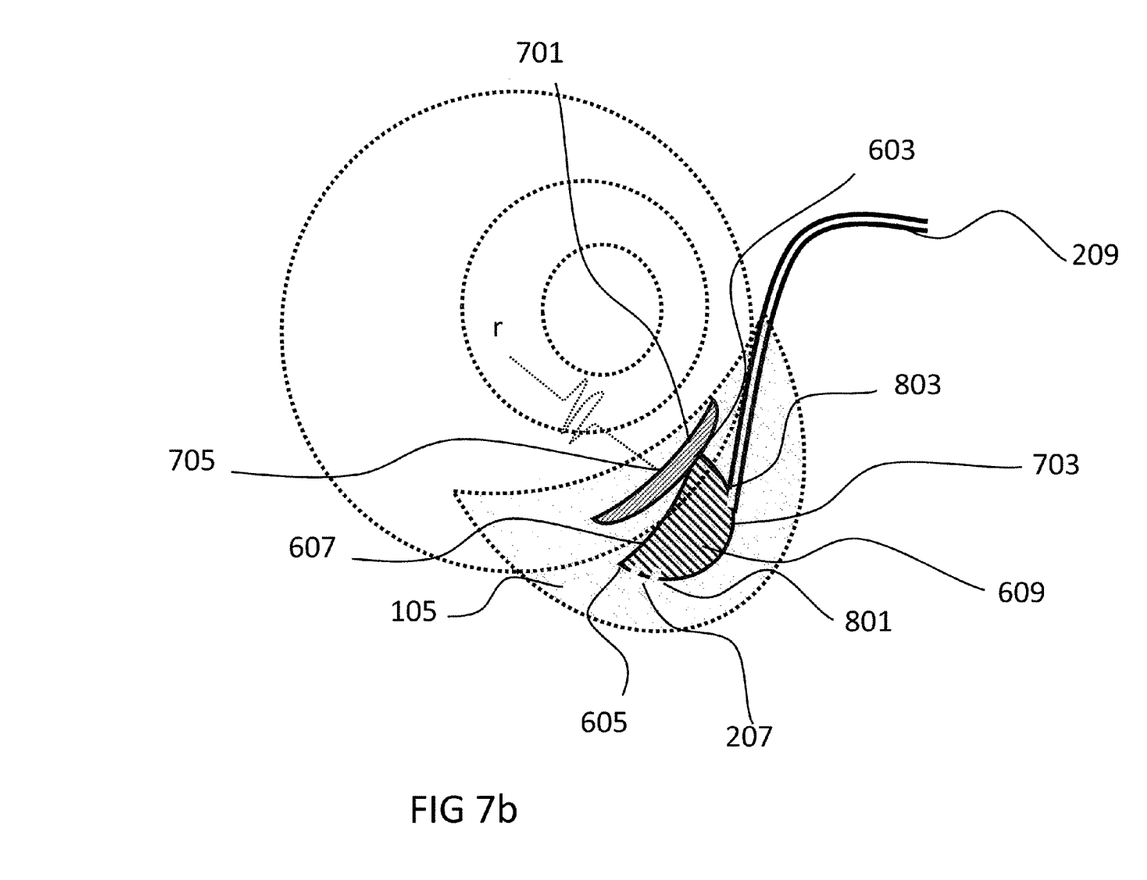

A similar distal portion 201 augmented with an outer rim 701 is shown in FIGS. 7a and 7b. This distal portion 201 comprises a reservoir 703 and an outer rim 701. The reservoir 703 has the same shape as the distal portion 201 represented in FIG. 6 and described above.

The outer rim 701 is placed on the upper crescent edge 603 of the reservoir 703, so as to avoid other parts of the distal portion 201, mainly the reservoir 703 or the tube 209, to hurt, irritate or wound the surface of the eye 111.

The reservoir 703 is the part of the distal portion 201 that bears the openings 207. The reservoir 703 is reservoir shaped, essentially hollow. The reservoir 703 itself can be used as a collection vessel 203 thanks to its configuration which is adapted for its function.

The reservoir 703 is made of a Shore A hardness material part 801 ranging between 5 and 60, preferably between 5 and 25. The reservoir 703 can also comprise a harder thermoplastic material part 803, to avoid the reservoir to collapse from the effect of the vacuum. This harder thermoplastic material part 803 can be placed at the end of the reservoir 703 which is linked to the tube 209, away from the openings 207. Many thermoplastic materials are suitable, such as PC, PMMA, PS, ABS, PET, POM, PBT, PVC, PE or PP, as long as these materials are biocompatible or suitable for medical applications.

The reservoir 703 thickness can vary, being minimal on limbus 113 side and close to the openings 207, and maximal away from limbus 113 and openings 207, close to the tube 209. Such a configuration strengthens the reservoir 703 structure, avoiding risks of collapsing due to the vacuum created by the suction means 210.

Example of method

The sampling device allows methods of tear fluid analysis to be realized.

Figure 8A:
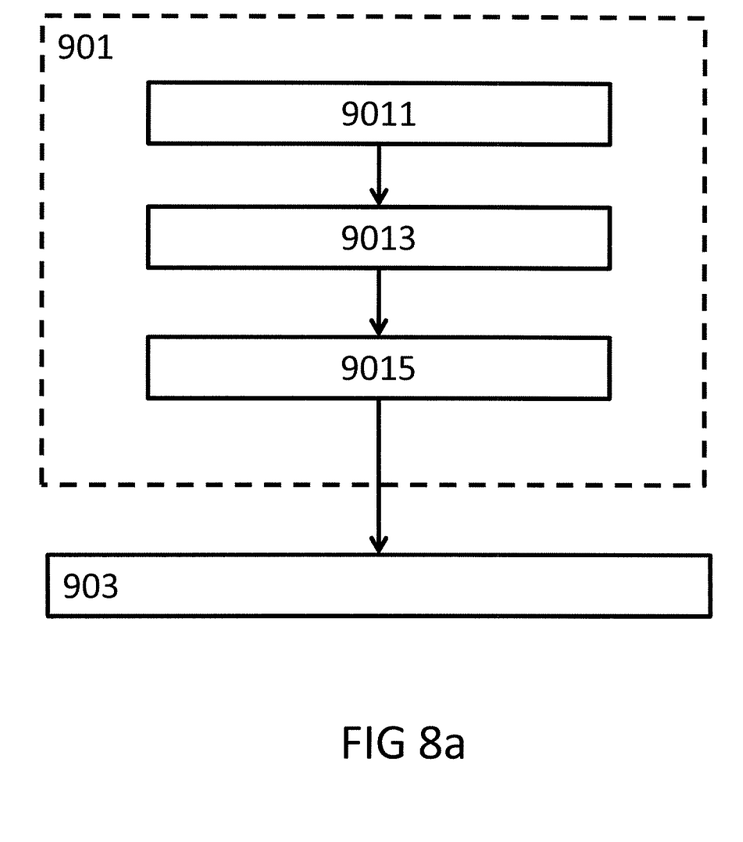

FIG. 8a represents a method of tear fluid analysis. The method comprises a sampling 901 of tear fluid by a device according to the above description. The sampling 901 first comprises a step 9011 of placing the extraction element 202 in the conjunctival sac 107. Then the step 9013 of continuous sampling is done on an extended period, at least 10 minutes, about one hour on average, thus providing the eye enough time to produce tear fluid, may the patient be suffering from KCS. This long step 9013 of continuous sampling also allows a better quality sample for analysis. The duration of the step 9013 indeed reduces variation and averages the sample composition. Finally the step 9015 of removing the extraction element 202 is performed, ending the sampling step 901. The sampling step 901 in itself requires minimal human operation, and particularly no medical personnel specific interaction during the sampling period.

The method then comprises a step of analysis 903 of the tear sample. A sample thus obtained is sufficient in quantity and in quality to be subject to many typical tear fluid analyses, for instance analyses useful for KCS diagnosis. Indeed, the method allows a sampling of at least 20 μl in case of extreme dryness, and an average 80 μl to 100 μl without extra efforts. Analyses such as osmolarity, IgE or proteomic analyses can be applied to a sample obtained with a device according to above description.

Figure 8B:
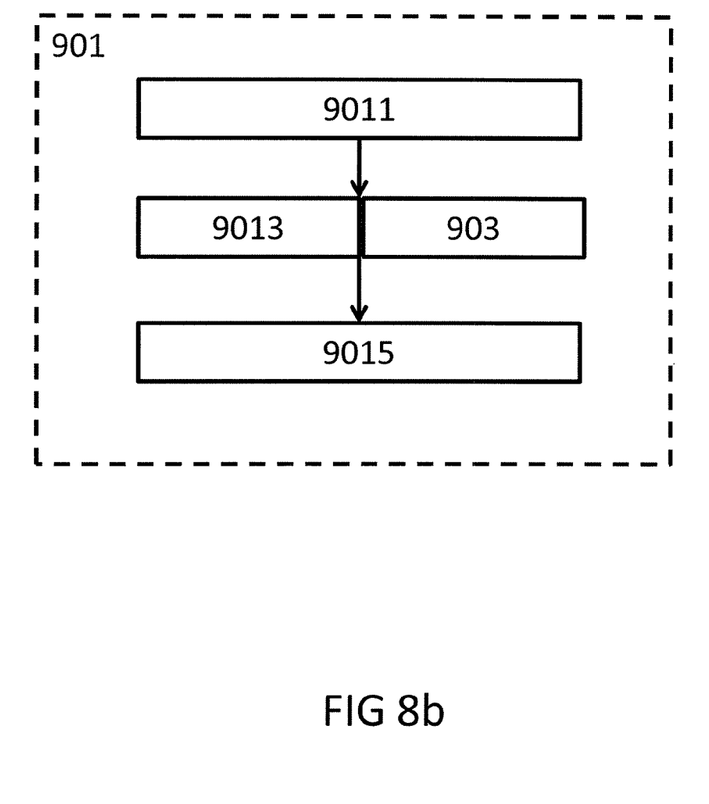

FIG. 8b represents another method of tear fluid analysis. In this method, the step of analysis 903 of the tear sample is be performed during the step 9013 of continuous sampling to allow continuous measurement of biological markers as a function of time, using methods such as microfluidics. This method benefits from a mean effects, as measurements are performed regularly throughout the step 9013 of continuous sampling.

The invention claimed is:

1. Device for sampling tear fluid, comprising:
an extraction element adapted to be applied on the eye to draw tear fluid therefrom, said extraction element including at least one tube and a distal portion,
a collection vessel, connected to one of said tube and said distal portion,
suction means adapted to continuously draw tear fluid from the eye to the collection vessel, through the extraction element for a period greater than 10 minutes once the extraction element is in place,
wherein the distal portion is configured to be positioned into a conjunctival sac of the eye and the extraction element removes tear fluid which resides in the conjunctival sac,
wherein the distal portion presents one inner curved side facing the surface of the eye situated under the lower eyelid and one outer curved side facing the lower eyelid, the inner curved side and outer curved side curvatures being chosen in order to correspond respectively to the curvature of the surface of the eye situated under the lower eyelid and to the curvature of the posterior surface of the lower eyelid, and
wherein the distal portion is linked to the collection vessel through a flexible tube.

2. Sampling device according to claim 1, wherein the distal portion (201) comprises an outer rim (701), said outer rim (701) being adapted to be positioned on the surface of the eye (111) situated under the lower eyelid (105).

3. Sampling device according to claim 1, wherein the distal portion includes the collection vessel.

4. Sampling device according to claim 1, wherein the tube is a flexible catheter and said distal portion includes perforations.

5. Sampling device according to claim 1, wherein the distal portion has a thickness that ranges between 0.5 and 3 mm and has a part adapted to be in contact with of the curvature eye in that the part has a radius (r) of curvature that ranges between 10 and 14 mm.

6. Sampling device according to claim 1, wherein the collection vessel comprises a first vessel opening allowing in tear fluid from the extraction element and a second vessel opening (219) linked to the suction means drawing air out, said second vessel opening being adapted not to allow tear fluid out.

7. Sampling device according to claim 1, wherein the collection vessel is a microfuge tube and/or has an internal volume higher than 20 μL.

8. Sampling device according to claim 1, wherein the collection vessel includes the suction means and the collection vessel is evacuated before the sampling.

9. Sampling device according to claim 1, wherein the collection vessel comprises fastening means adapted to fasten said collection vessel on the face of the subject, in the vicinity of a temporal palpebral fissure.

10. Sampling device according to claim 1, wherein the device comprises a vacuum gauge.

11. Sampling device according to claim 1, wherein the suction means comprise a pump.

12. Sampling device according to claim 1, wherein the suction means comprise a three ways non-return valve, one nonreturn way allowing air from the collection vessel and one other non-return way drawing air out of said valve, last way being linked to a plunger assembly, said plunger assembly being successively pushed and pushed back.

13. The device of claim 1, wherein a junction between the two lateral curved sides corresponds to a lower crescent edge.

14. The device of claim 1, wherein the suction means include a plunger assembly.

15. Device for sampling tear fluid, comprising:
an extraction element adapted to be applied on the eye to draw tear fluid therefrom, said extraction element including at least one tube and a distal portion,
a collection vessel, connected to one of said tube and said distal portion,
suction means adapted to continuously draw tear fluid from the eye to the collection vessel, through the extraction element for a period higher than 10 minutes once the extraction element is in place,
wherein the distal portion is configured to be placed within a conjunctival sac of the eye and the extraction element removes tear fluid which resides in the conjunctival sac,
wherein the distal portion includes an outer annular sector side and an inner annular sector side facing each other, wherein the outer annular sector side faces the lower eyelid while the inner sector side faces the surface of the eye,
wherein the distal portion is linked to the collection vessel by a flexible tube.

16. The device of claim 15, wherein the distal portion has a vertical section in the shape of a sector.

17. The device of claim 16, wherein a lower arcuate side of the distal portion is formed by arcs of sector shaped vertical sections.

18. The device of claim 15, wherein the suction means include a plunger assembly.

* * * * *